United States Patent [19]
Guevara, Jr.

[11] Patent Number: 4,729,823
[45] Date of Patent: Mar. 8, 1988

[54] APPARATUS AND METHODS FOR ELECTROPHORESIS

[75] Inventor: Juan G. Guevara, Jr., Houston, Tex.

[73] Assignee: Guevara-Kelley Scientific Products, Inc., Houston, Tex.

[21] Appl. No.: 894,886

[22] Filed: Aug. 8, 1986

[51] Int. Cl.$^4$ ............................................. G01N 27/26
[52] U.S. Cl. ............................ 204/299 R; 204/182.8
[58] Field of Search .............. 204/182.8, 182.9, 299 R

[56] References Cited

U.S. PATENT DOCUMENTS

| | | | |
|---|---|---|---|
| 3,129,158 | 4/1964 | Raymond et al. | 204/299 R |
| 3,197,393 | 7/1965 | McEven | 204/299 R |
| 3,208,929 | 9/1965 | Raymond et al. | 204/299 R |
| 3,773,648 | 3/1987 | Van Welzen et al. | 204/299 R |
| 4,459,158 | 7/1984 | Mizuno et al. | 204/299 R |
| 4,576,693 | 3/1986 | Kreisher et al. | 204/299 R |

Primary Examiner—John F. Niebling
Assistant Examiner—John S. Starsiak, Jr.
Attorney, Agent, or Firm—David M. Ostfeld

[57] ABSTRACT

An apparatus and methods are provided for separating components from a mixture utilizing electrophoresis. The apparatus comprises a means for separating the components which also concentrates the components as they are separated from the mixture. The means for separating is provided with additional heat exchange surface for improved heat exchange with the separation medium. These features result in improved resolution within the apparatus and improved quality of the results therefrom.

4 Claims, 4 Drawing Figures

APPARATUS AND METHODS FOR ELECTROPHORESIS

BACKGROUND OF THE INVENTION

The present invention relates generally to apparatus and methods for separating individual components from a mixture; more particularly, it relates to apparatus and methods which separate such components by the use of electrophoresis.

The term electrophoresis is generally used to describe the migration of a suspended particle in an electric field. The principles of electrophoresis have long been known but have only more recently been used extensively in separations technology.

Of particular importance is the use of electrophoresis to separate materials of biological origin for examination, particularly molecules of high molecular weight such as, for example, proteins, enzymes, nucleic acids, complex lipids and other carbohydrates. It is highly desirable when separating such materials to cause as little damage to or alter the molecules so that their properties are not changed significantly for analysis. The use of electrophoresis provides one significant means of accomplishing this.

There are apparatus available for performing separation by electrophoresis. Most generally comprise two electrodes with a separation chamber having a separating matrix therein, usually a gel, interposed between the electrodes. The components of the mixture migrate at different flow rates through this matrix under the influence of an applied electric field, with the different components emerging from the separating chamber one after the other.

These components are collected for sampling and analysis usually by one of two methods. The apparatus may be allowed to run for a specified period of time after which the components are collected directly from the matrix, or the components are allowed to flow completely through the matrix and into an elution chamber where they carried out by a flowing buffer solution.

Originally the separating matrix utilized in electrophoresis apparatus was a free solution (free-flow electrophoresis); however, the free-flow systems were impaired greatly by thermal convection and sedimentation within the free-flow medium. This technology has now been largely supplanted by the use of supporting mediums, particularly gels. The purpose of the supporting medium is to decrease the flow currents within the medium so that the separated components remain as sharp zones with maximum resolution between these zones. The supporting mediums are preferably chemically inert during the electrophoresis operations, generally uniform in their properties and able to be readily prepared and reproduced. Two of the more common supporting mediums are polyacrylamide gels and aragose gels.

As previously mentioned, a great variety of apparatus exist for carrying out electrophoresis. Most only significantly differ in their construction of the separating chamber. Two basic separating chamber designs currently prevail: cylindrical gel columns and slab gel designs. For example, U.S. Pat. No. 4,111,785 discloses a particular electrophoresis apparatus utilizing a cylindrical gel column separating chamber (the apparatus is currently manufactured and sold through Bethesda Research Laboratories, Gaithersburg, Md.). Also, U.S. Pat. Nos. 4,088,561 and 4,130,471 disclose particular electrophoresis apparatus utilizing slab gel separating chambers.

These apparatus, however, suffer from many shortcomings. For example, the cylindrical gel columns only provide limited resolution for low concentration components and are subject to overheating. Overheating of the gel column results in loss of stability and uniformity within the separating media, distortion between the zones of separation and loss of resolution within the system. Because of this overheating problem, the size of the cylindrical gel columns and the amount of power supplied thereto is limited. Further, cylindrical gel columns are generally cumbersome, difficult to assemble, complex to operate and somewhat unsafe during operation. Slab gel columns suffer from these same shortcomings plus they require a large volume of buffer solution to be used, further diluting the components and lowering the resolution of the system.

It is therefore an object of the present invention to provide an electrophoresis apparatus and method of operation for not only separating individual components from a mixture, but also concentrating those components as they are separated within the apparatus to improve the resolution of the apparatus and quality of results therefrom.

It is a further object of the present invention to provide an electrophoresis apparatus having improved heat exchange capability within the gel column so that higher power levels can be utilized within the apparatus without loss of resolution or decreased quality of results.

It is a still further object of the present invention to provide an electrophoresis apparatus of relatively simple construction, which is uncomplicated to use, and which is also safer to operate.

SUMMARY OF THE INVENTION

In accordance with the present invention, There is provided apparatus and methods for electrophoresis. The apparatus, in its overall concept, comprises a means for separating components from a mixture, the means being interposed between an upper and lower buffer reservoir having electrodes therein, the means further being constructed so as to concentrate the components as they are separated within the means to provide improved resolution of the apparatus and improved quality of results therefrom. The means for separating more preferably is constructed of a shape having a decreased diameter from a first end to a second end thereof, still more preferably of a generally conical, parabolic or hemispherical shape.

The means for separating preferably comprises a hollow outer frustum and an inner member spaced apart from the interior of the hollow frustum, the frustum and the inner member cooperating to form a column therebetween, with the column being of a shape so as to concentrate the components of the mixture as they are separated within the column. The frustum and the inner member are more preferably of a shape having a decreased diameter from a first end to a second end thereof. The frustum and the inner member are still more preferably of a generally conical or hemispherical shape.

Because of the construction of the means for separating, the gel column will have a decreased diameter and decreased cross-sectional area along its length. This decreased cross-sectional area results in a decreased volume of gel per unit length in the gel column. As concentration is inversely proportional to volume, a constant mass in a decreased volume will produce an increased concentration. The apparatus of the present invention, therefore, allows components having small concentrations within a mixture to not only be separated from the mixture but also concentrated for collection. This feature improves both the resolution of the apparatus and the quality of the samples collected therefrom.

The inner member further preferably has a cavity extending therein, this cavity providing additional heat exchange surface with the gel column allowing more power to be run through the gel column without a significant decrease in the resolution of the apparatus of the present invention or the quality of results therefrom.

The electrophoresis apparatus further preferably comprises an elution chamber for removing the separated components from the gel column, and a means for recycling the buffer solution in the upper and lower buffer reservoirs therebetween.

The apparatus of the present invention is applicable for use in a wide variety of electrophoresis separations such as, for example, the separation of proteins or nucleic acids from a mixture of the same. The methods of the present invention provide the procedure for performing such operations.

These and other features and advantages of the present invention will be more readily understood by those skilled in the art from a reading of the following detailed description with reference to the accompanying drawings.

DETAILED DESCRIPTION OF THE PREFERRED EMBODIMENT

Figure 1:
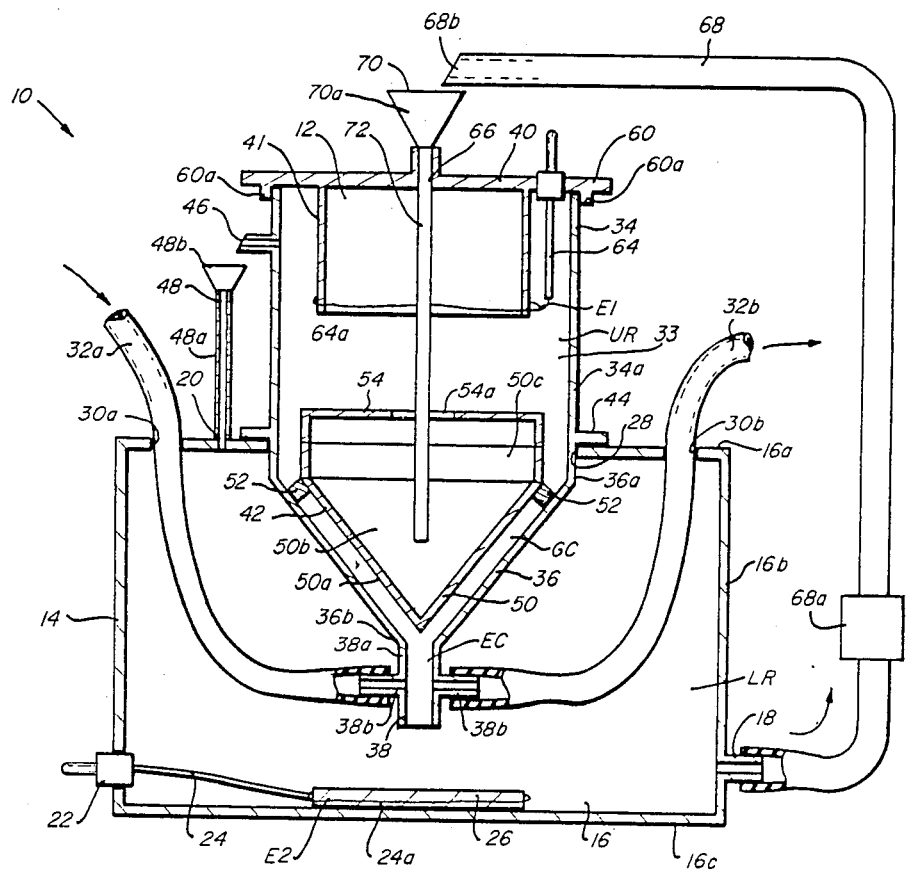
FIG. 1 is a cross-sectional elevation of an electrophoresis apparatus in accordance with the present invention.

Referring now to the drawings in more detail, particularly to FIG. 1, there is illustrated a cross-sectional elevation of an electrophoresis apparatus 10 in accordance with the present invention. Apparatus 10 generally comprises an upper buffer reservoir UR, an upper electrode E1, a gel column GC, an elution chamber EC, a lower buffer reservoir LR and a lower electrode E2. As illustrated in FIG. 1, upper buffer reservoir UR, upper electrode E1, gel column GC and elution chamber EC are included in the top section 12 of apparatus 10, while lower buffer reservoir LR and lower electrode E2 are included in the bottom section 14 of apparatus 10.

Figure 2:
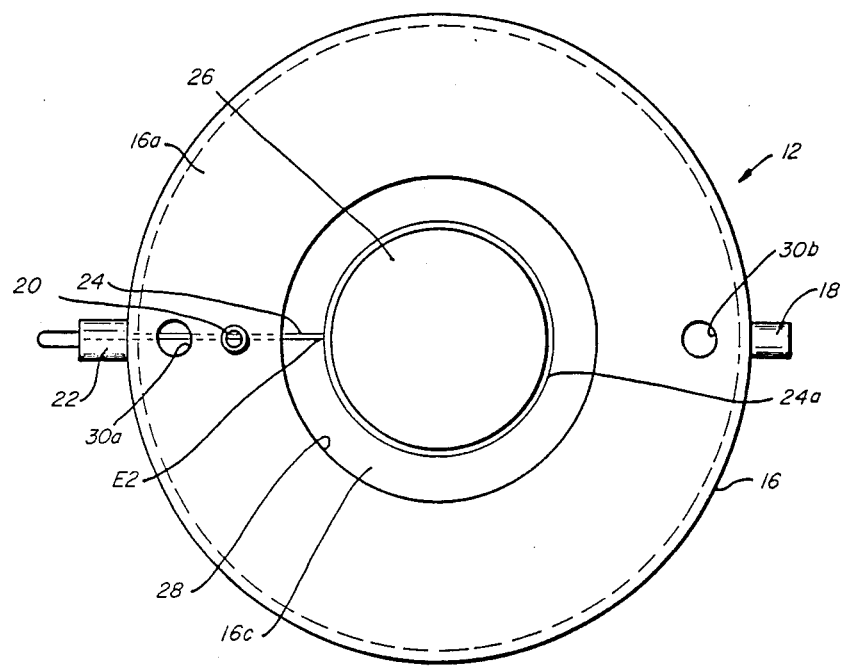
FIG. 2 is a top view of the bottom section of the apparatus of FIG. 1.

Referring now to FIGS. 1 and 2, bottom section 14 comprises a hollow container 16 which functions as lower buffer reservoir LR. Container 16 is preferably a hollow cylinder having a top wall 16a, side wall 16b and base 16c. Container 16, however, may be of any shape suitable for acting as such a reservoir as will be recognized by those skilled in the art.

Side wall 16b of container 16 has a fluid outlet port 18 extending therefrom proximate base 16c, outlet port 18 being utilized as an outlet for buffer solution recycled from lower buffer reservoir LR to upper buffer reservoir UR as detailed later. Side wall 16b further has an electrical port 22 proximate base 16c to which lower electrode E2 is connected. As illustrated in FIG. 1, port 22 is a banana-type plug; however, port 22 may be any electrical port known to those skilled in the art capable of electrically interfacing lower electrode E2 with a power source (not shown). Lower electrode E2 preferably comprises a highly conductive wire 24 such as, for example, platinum wire, extending from port 22 into lower reservoir LR and having a loop 24a at its end. Loop 24a is provided so that a uniform current will flow across gel column GC during electrophoresis operations to assure uniform separation, as detailed below. Wire 24 is preferably insulated from port 22 to loop 24a for this same reason.

Base 16c optionally includes a plateau 26, which preferably comprises a raised cylindrical piece centrally oriented on base 16c inside lower buffer reservoir LR. Loop 24a of wire 24, in turn, is placed around plateau 26. Plateau 26 acts to direct any gases present in lower buffer reservoir LR such as, for example, hydrogen or oxygen resulting from the electrolysis of the buffer solution, away from the base of stem 38 of top section 12. Gases trapped at the base of stem 38 can affect the degree of resolution obtainable using apparatus 10, so it is desirable to minimize their presence. Plateau 26 also acts as a stable, central mount for loop 24a of wire 24 to insure a uniform current across gel column GC and to minimize any accidental movement of loop 24a during the operation of apparatus 10.

Top wall 16a of container 16 has a central bore 28 through which top section 12 is inserted and rests when apparatus 10 is in operation. Top wall 16a also has bores 30a and 30b through which sample tubes 32a and 32b, respectively, extend. Sample tubes 32a and 32b are attached to elution chamber EC for sample collection as further detailed below. Top wall 16a still further has a fluid inlet port 20 extending out therefrom which is utilized as an inlet for buffer solution draining from upper buffer reservoir UR into lower buffer reservoir LR. The purpose of the upper reservoir drain is also detailed below.

As just mentioned, top section 12 extends into container 16 through bore 28 in top wall 16a. Referring again to FIG. 1, top section 12 preferably comprises a funnel 33 having an extended upper section 34, a mid-section 36 and stem 38. Top section 12 further comprises a cover 40 for covering extended upper section 34, and an inner member 42 placed within funnel 33 spaced apart from mid-section 36 as detailed below.

Extended upper section 34 preferably comprises a hollow cylinder open at its top, connected to mid-section 36 at its base, and having a side wall 34a interposed between. Side wall 34a is provided with a flange 44 for use in mounting top section 12 onto top wall 16a of bottom section 14, flange 44 acting to limit the extension of top section 12 into lower buffer reservoir LR.

Side wall 34a also has a fluid outlet port 46 for use in conjunction with fluid inlet port 20 of bottom section 14. Ports 20 and 46 are preferably connected via a discontinuous drain system 48 which allows buffer solution in upper buffer reservoir UR to drain into lower buffer reservoir LR without the formation of an electrical circuit across this path. If such a circuit were allowed to form, the electrical flow across gel column GC would be greatly reduced because of a lower electrical resistance around gel column GC. As depicted in FIG. 1, discontinuous drain system 48 utilizes a funnel 48a mounted on an inlet tube 48b attached to port 20, funnel 48a collecting buffer solution flowing out the end of port 46. Discontinuous drain system 48, however, may be any means known to those skilled in the art which will allow the buffer solution in upper buffer reservoir UR to flow into lower buffer reservoir LR while avoiding the formation of an electrical circuit across this path.

Side wall 34a of upper section 34, when top section 12 is mounted with bottom section 14, extends slightly below top wall 16a of container 16, where side wall 34a becomes mid-section 36. Mid-section 36 preferably comprises a frustum having a decreased diameter from its top 36a to its base 36b. Most preferably, midsection 36 is of a frusto-conical shape; however, mid-section 36 may be frusto-hemispherical, frusto-parabolic or any other conforming shape.

Stem 38 extends from base 36b of mid-section 36. Stem 38 functions as elution chamber EC wherein the samples separated by the electrophoresis process are removed for collection as detailed below. Stem 38 preferably comprises a hollow t-shaped extension from mid-section 36. The hollow vertical extension 38a extends from the interior of top section 12 (the base of gel column GC) into lower buffer reservoir LR. The hollow horizontal extensions 38b extend out from hollow vertical extension 38a perpendicular thereto. During the operation of apparatus 10, sample tube 32a is attached to one of hollow horizontal extensions 38b and another sample tube 32b is attached to the other. Buffer solution from an external buffer reservoir (not shown) is drawn through tube 32a and the corresponding one of hollow horizontal extensions 38b into hollow vertical extension 38a. Samples which have entered hollow vertical extension 38a from gel column GC are washed out by this buffer solution and exit through the other one of hollow horizontal extensions 38b and sample tube 32b into a collection reservoir (not shown) for collection and analysis. This sample collection process is further detailed below in the discussion of the operation of apparatus 10.

Figure 3:
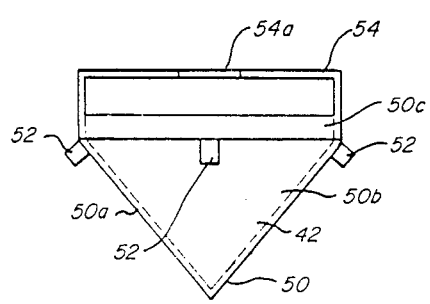
FIG. 3 is an elevational view of the inner member of the apparatus of FIG. 1.
Figure 4:
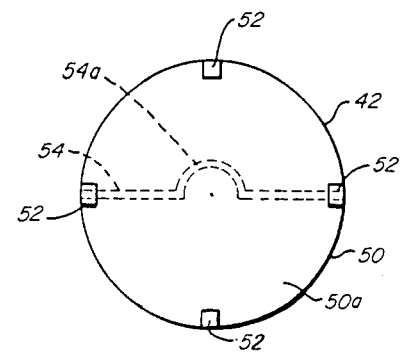
FIG. 4 is a bottom view of the inner member of FIGS. 1 and 3.

As previously mentioned, inner member 42 is placed within top section 12 spaced apart from mid-section 36. Inner member 42 is constructed of the same general shape as mid-section 36. As depicted in FIGS. 1, 3 and 4, inner member 42 comprises a cone 50 since mid-section 36 is of a generally conical shape. Inner member 42, however, could also be comprise a hemispherical, parabolic or other shape if mid-section 36 is of that shape.

Cone 50 has a plurality of spacers 52 mounted on the exterior surface 50a thereof. In the alternative, spacers 52 could be mounted on the interior wall of mid-section 36. When cone 50 is in place within top section 12, spacers 52 are in contact with the interior wall of mid-section 36, resulting in inner member 42 being spaced apart from mid-section 36. Gel column GC is formed in this space between inner conical member 42 and mid-section 36.

Because of the aforementioned construction of inner member 42 and mid-section 36, gel column GC will have a decreased diameter and decreased cross-sectional area along its length, a major feature of the present invention. This decreased cross-sectional area results in a decreased volume of gel per unit length in gel column GC. As concentration is inversely proportional to volume, a constant mass in a decreased volume will produce an increased concentration. Apparatus 10, therefore, allows components having small concentrations within a mixture to not only be separated from the mixture but also concentrated for collection. This feature improves both the resolution of apparatus 10 and the quality of the samples collected therefrom.

Cone 50 is preferably provided with a cavity 50b therein, cavity 50b preferably being as large as possible without affecting the structural integrity of cone 50. Cavity 50b is another major feature of the present invention as it provides an increased surface area for heat exchange with gel column GC. As previously mentioned, when the temperature increases within the gel column, the resolution of the apparatus and the quality of results decrease significantly. The additional heat exchange surface provided by cavity 50b allows more power to be used with apparatus 10 to significantly decrease the processing time of a sample without significantly decreasing the quality of the results. Cone 50 is also preferably provided with a cylindrical upper wall 50c to prevent samples placed on gel column GC for separation from falling into cavity 50b, and a handle 54 for ease of insertion and removal of cone 50 from top section 12.

Referring again to FIG. 1, cover 40 is provided to be placed over the top of extended upper section 34 of top section 12. Cover 40 preferably comprises a disc 60 having flanges 60a extending from the base of disc 60. Flanges 60a are provided to fit around the exterior of cylindrical side wall 34a of upper extended section 34 to secure disc 60 in place thereon.

Cover 40 also has an electrical port mounted therein proximate the inside of side wall 34a of upper section 34, port 62 having upper electrode E1 connected thereto. As illustrated in FIG. 1, port 62 is a banana-type plug; however, port 62, like port 22, may be any electrical port known to those skilled in the art capable of electrically interfacing upper electrode E1 with a power source (not shown). Upper electrode E1 preferably comprises a highly conductive wire 64 such as, for example, platinum wire, extending from port 62 into upper buffer reservoir UR and having a loop 64a at its end. Loop 64a preferably has an identical construction to loop 24a to ensure the uniform current across gel column GC. Wire 64 must be of sufficient length to extend into the buffer solution, that is, below fluid outlet port 46, in upper reservoir UR to complete the electrical circuit across gel column GC for the electrophoresis operations. Wire 64, like wire 24, is preferably insulated from port 62 to loop 64a.

Cover 40 optionally includes a hollow cylindrical extension 41 extending into upper buffer reservoir UR which, like plateau 26, is provided to act as a stable, central mount for loop 64a of wire 64 to insure a uniform current across gel column GC and to minimize any accidental movement of loop 64a.

Cover 40 also has a fluid inlet port 66 which, in conjunction with fluid outlet port 18 of bottom section 12, is used in recycling buffer solution from lower buffer reservoir LR to upper buffer reservoir UR. Recycle tube 68 connects fluid outlet port 18 to fluid inlet port 66, with pump 68a interposed along recycle tube 68 between fluid outlet port 18 and fluid inlet port 66 to pump the buffer solution from lower buffer reservoir LR to upper buffer reservoir UR. Pump 68a may be any pump known to those skilled in the art capable of pumping buffer solution at consistent, low flow rates such as, for example, a peristaltic or centrifugal pump.

The buffer recycle loop is preferably provided with a discontinuous drain system 70 for the same reasons as detailed in the discussion of discontinuous drain system 48. As depicted in FIG. 1, discontinuous drain system 70 utilizes a funnel 70a attached to fluid inlet port 66 to gather fluid discharged from the end 68b of recycle tube 68; however, discontinuous drain system 70 may be any such system known to those skilled in the art as discussed previously.

Preferably attached to inlet port 66 and extending into cavity 50b of cone 50 is inlet recycle tube 72. Inlet recycle tube 72 extends into cavity 50b both to minimize turbulence within upper buffer reservoir UR and to assist in cooling gel column GC to improve the performance and resolution of apparatus 10. If inlet recycle tube 72 is so provided, handle 54 of cone 50 will be provided with a bend 54a to allow central passage of tube 72.

The construction of cover 40 is another of the many important features of apparatus 10. Particularly, the construction of upper electrode E1 allows the circuit across gel column GC to be broken merely by lifting cover 40 off extended upper section 34. This simple method of stopping the electrical flow through apparatus 10 greatly diminishes the risk of electrocution during its operation.

Apparatus 10 and its components may be constructed from a wide variety of materials. For example, the various components of apparatus 10 may be constructed of glass, plastic, rubber, metal or other materials as will be understood by those skilled in the art, and the actual materials of construction are not intended as a limitation on the present invention. It is preferred, however, that the components of apparatus 10, except of course electrode E1 and E2, be constructed of electrically non-conductive material to maximize the current flow through gel column GC.

The apparatus of the present invention is particularly useful in a variety of electrophoresis operations, most particularly separation through the use of gel electrophoresis. For example, apparatus 10 is particularly useful in separating proteins by molecular mass or electric properties under denaturing or non-denaturing conditions. As another example, apparatus 10 is particularly useful in the preparative electrophoresis of proteins or nucleic acids. Apparatus 10, therefore, may be adapted to almost any electrophoresis procedure.

In preparing apparatus 10 for electrophoresis operations, top section 12 and bottom section 14 are initially disassembled. The first step is to form gel column GC. Inner member 42 is inserted into top section 12 in place proximate mid-section 36. The particular gel composition chosen for gel column GC is then inlaid between inner member 42 and mid-section 36, the gel composition being any one of a number of well known gel compositions and gel column GC being formed by any one of a number of well known techniques. The actual composition and formation of gel column GC will depend upon a number of factors, all related to the specific separation to be performed. These factors include, but are not limited to, the types of mixtures to be separated and the component characteristics chosen as the basis for the separation. For example, polyacrylamide gels are normally used for the separation of proteins and aragose gels are normally used for the separation of nucleic acids. Those skilled in the art will recognize these factors and understand how to adjust the composition and preparation of gel column GC accordingly.

Once gel column GC is in place, top section 12 is mounted onto bottom section 14. Buffer solution is added to upper and lower buffer reservoirs UR and LR, respectively, lower buffer reservoir LR being filled to the level of mid-section 36 and upper buffer reservoir UR being filled to just below fluid outlet port 46. The actual buffer solution utilized with apparatus 10 will again vary on factors all of which are related to the specific electrophoresis separation desired. These factors again include, but are not limited to, the compositions of the specific mixtures to be separated and the component characteristics chosen as the basis for the separation. For example, tris-glycinesodium dodecyl sulfate (SDS), tris-barite-urea and tris-acetate solutions of varying pH are normally utilized for the separation of proteins. Those skilled in the art will again be able to recognize these factors and understand how to adjust the composition and pH of the buffer solutions accordingly.

The specific mixture to be separated is then introduced onto the top of gel column GC, and a current is applied across gel column GC with constant voltage. Recycle pump 68a is started causing the recycle of buffer solution from lower buffer reservoir LR to upper buffer reservoir UR. As upper buffer reservoir UR fills to the level of fluid outlet port 46, the buffer solution will drain out port 46 back into lower buffer reservoir LR.

As the current is applied across gel column GC, the components of the mixture begin migrating through gel column GC at varying rates toward elution chamber EC. As a specific component reaches elution chamber EC, buffer solution from an external buffer reservoir (not shown) flowing through sample tube 32a into elution chamber EC carries the component out of elution chamber EC through sample tube 32b and into a sample collector (not shown) for storage and/or analysis.

In the alternative to removing the separated components through elution chamber EC, apparatus 10 can be run for a predetermined period of time and stopped. Gel column GC can then be removed from apparatus 10 and analyzed by any one of a number of well known methods. The use of elution chamber EC, however, simplifies the separation and analysis procedure, and is preferred.

To more specifically illustrate the operation of apparatus 10, the following specific procedure for the separation of proteins from a mixture by molecular weight is given. The procedure utilizes a polyacrylamide gel as the separation medium (gel column GC) and tris-glycine-SDS as the buffer solution.

Gel column GC is first prepared. A small piece of parafilm is used to seal the base of hollow vertical extension 38a of stem 38 with an O-ring. Sample tubes 32a and 32b are then secured to hollow horizontal extensions 38b, and funnel 33 is secured to a ring stand and leveled.

A solution of 18% acrylamide having a pH of about 8.6 is poured into stem 38 up to hollow horizontal extensions 38b. The acrylamide solution is overlaid with an alcohol, preferably butanol, to provide a level surface on the acrylamide solution, and the acylamide is allowed to polymerize to form a lower plug. The 18% acrylamide will produce a relatively non-porous plug to prevent components entering elution chamber EC from leaking out the base thereof. Once polymerized, the polyacrylamide plug is washed thoroughly with water to remove the alcohol.

A syringe containing 50% glycerol and water bromophenol blue dye is attached to sample tube 32a and both tubes are filled with this solution. The syringe is kept in place while sample tube 32b is clamped using a hemostat or a small C-clamp. The level of glycerol solution is brought to a small distance above hollow horizontal extensions 38b.

A solution of 3.5% acrylamide having a pH of about 8.6 is layered onto the glycerol solution up to the conjuncture of gel column GC and stem 38. The glycerol solution keeps the acrylamide from entering hollow horizontal extensions 38b to prevent their plugging. This acrylamide solution is again covered with an alcohol, preferably butanol, to provide a level surface on the solution, and the acrylamide is allowed to polymerize to form an upper plug. The 3.5% acrylamide solution will form a relatively pourous plug to allow components exiting gel column GC easy access into elution chamber EC. Once polymerized, this polyacrylamide plug is washed with water as before to remove the alcohol.

Inner member 42 is then placed within top section 12 with the tip of inner member 42 being in contact with the upper plug. The clamp on sample tube 32a is removed and the remaining glycerol solution in the syringe is gently pushed through the chamber formed between the two plugs to insure that hollow horizontal extensions 38b are not plugged. Once the glycerol solution has been pushed through, the chamber is washed with water and filled with the tris-glycine-SDS electrolyte buffer. This buffer should be pumped through elution chamber EC to ensure that air bubbles are not introduced into elution chamber EC and any air already therein is removed.

The acrylamide solution utilized as the separating gel is next introduced into gel column GC. The composition of the acrylamide solution will vary depending upon the molecule size within the protein mixture, and one skilled in the art will be able to make adjustments to the solutions accordingly. For example, 3% to 5% acrylamide solutions are preferred for molecular weights over 100,000, 5% to 12% acrylamide solutions are preferred for molecular weights between 20,000 and 150,000, 10% to 15% acrylamide solutions are preferred for molecular weights between 10,000 and 80,000, and over 15% acrylamide solutions are preferred for molecular weights under 15,000. Once in place, the solution is covered with a layer of alcohol, preferably butanol, as with the other acrylamide solutions and allowed to polymerize. Once polymerized, the gel is washed with water to remove the alcohol.

Once the gel has been polymerized within the gel column GC, top section 12 is mounted onto bottom section 14. A tris-glycine-SDS buffer solution of about pH 8.6 is added to lower buffer reservoir LR up to the level of gel column GC, and the same buffer solution is added to upper buffer reservoir to just below fluid outlet port 46. Cover 40 is placed onto extended upper section 34 and recycle pump 68a is started and adjusted for the desired recycle flow rate.

Electrodes E1 and E2 are then connected to a direct current power supply (not shown) with upper electrode E1 preferably being the cathode and lower electrode E2 preferably being the anode. The system is allowed to run for about one hour to remove any contaminant ions from the top of gel column GC where the protein mixture will be placed.

After this hour, the power supply is disconnected and recycle pump 68a is stopped. Cover 40 is removed from extended upper section 34 and the protein mixture having 0.005% bromophenol blue dye and 10% glycerol is introduced onto the top of gel column GC. This is accomplished using a long, narrow pipette or syringe having a long needle, and is done carefully to minimize the mixing of the sample mixture and buffer solution in upper buffer reservoir UR. Cover 40 is then replaced on extended upper section 34 and the power supply is reattached and maintained for about one hour to minimize disturbance of the protein mixture and to insure migration of the protein mixture into the gel. After this hour, recycle pump 68 is restarted.

The bromophenol blue dye is utilized to monitor the migration through the gel in gel column GC. The dye is a negatively charged, small molecular mass compound that will migrate through the gel well in front of the protein mixture. The migration of the dye is used to determine the flow rate of the buffer solution through elution chamber EC for sample collection as will be understood by those skilled in the art. Samples are then collected from elution chamber EC as desired and under conditions suitable for the specific experiment.

The apparatus and methods of the present invention provide electrophoresis operations having improved resolution, improved heat exchange ability for the gel column, lower separation times and higher overall quality of results. The apparatus provides a simple and highly effective means for performing the electrophoresis separations, and the methods utilize the apparatus to significantly increase the quality of the results.

First, the construction of the gel column GC concentrates the individual components separated from the mixture as those components flow down gel column GC. This allows components very dilute in the original mixture to be identified with greater accuracy, thereby improving the resolution of the apparatus.

Further, the construction of inner member 42 allows greater power levels to be used within the apparatus to accelerate the separation without any significant loss in resolution or quality. Cavity 50b provides the gel column with a greatly increased area for heat exchange, and with the flow of buffer solution through cavity 50b, a greater amount of heat can be removed therefrom. This improved heat exchange not only improves the performance of gel column GC as a separation medium but also allows higher power levels to be used which would ordinarily be adverse to the results.

Still further, the construction of cover 40 allows the electrical circuit to be broken merely by removing cover 40 from of top section 12. Not only does this feature provide a quick method of shutting off the process in case of emergency, it also greatly reduces the risk of electrocution in such instances.

Many modifications and variations besides the embodiments specifically mentioned may be made in the techniques and structures without departing substantially from the concept of the present invention. Accordingly, it should be clearly understood that the form of the invention described and illustrated herein is exemplary only, and is not intended as a limitation on the scope thereof.

I claim:

1. An apparatus for separating individual components from a mixture of said components by electrophoresis, comprising:

a first buffer reservoir for holding a buffer solution;

a positive electrode within said first buffer reservoir in electrical contact with said buffer solution therein;

a second buffer reservoir for holding said buffer solution;

a negative electrode within said second buffer reservoir in electrical contact with said buffer solution therein;

means for separating said components from said mixture, wherein said means for separating is interposed between said first and second reservoirs, and wherein said means for separating comprises:

a hollow out frustum, an inner member spaced apart from an interior surface of said hollow frustum to form a column therebetween, and a separation medium within said column, wherein said components are separated from said mixture as said components migrate through said separation medium from a first end of said column toward a second end thereof, wherein said column is constructed so that said components are concentrated as they migrate through said separation medium, and wherein said inner member provides additional heat exchange surface to remove heat from said separation medium, and recycle means for recycling said buffer solution in a path between said first reservoir and said second reservoir without a formation of an electrical circuit across said path.

2. An electrophoresis apparatus, comprising:

an upper buffer reservoir for holding a buffer solution;

an upper electrode within said upper buffer reservoir in electrical contact with said buffer solution therein a lower buffer reservoir for holding said buffer solution;

a lower electrode within said lower buffer reservoir in electrical contact with said buffer solution therein;

means for defining a gel column, said means being interposed between said upper and lower buffer reservoirs and further interposed between said upper and lower electrodes, said means comprising:

a hollow outer frustum, an inner member spaced apart from an interior surface of said hollow outer frustum to form said gel column therebetween, wherein said gel column is in electrical contact with said upper and lower electrodes, wherein said gel column is constructed of a shape having a decreased diameter along the length thereof, and wherein said inner member provides additional heat exchange surface to remove heat from said gel column, and wherein said hollow frustum has a plurality of spacers on said interior thereof to space said inner member apart from said interior of said hollow frustum.

3. An electrophoresis apparatus, comprising:

an upper buffer reservoir for holding a buffer solution;

an upper electrode within said upper buffer reservoir in electrical contact with said buffer solution therein;

a lower buffer reservoir for holding said buffer solution;

a lower electrode within said lower buffer reservoir in electrical contact with said buffer solution therein; and means for defining a gel column, said means being interposed between said upper and lower buffer reservoirs and further interposed between said upper and lower electrodes, said means comprising:

a hollow outer frustum, and an inner member spaced apart from an interior surface of said hollow outer frustum to form said gel column therebetween, wherein said gel column is in electrical contact with said upper and lower electrodes, wherein said gel column is constructed of a shape having a decreased diameter along the length thereof, and wherein said inner member provides additional heat exchange surface to remove heat from said gel column, and means for recycling said buffer solution in a path between said lower buffer reservoir and said upper buffer reservoir without a formation of an electrical circuit across said path.

4. An electrophoresis apparatus for separating a component from a mixture under the influence of an electrical current, comprising:

an upper buffer reservoir for holding a buffer solution;

an upper electrode within said upper buffer reservoir in electrical contact with said buffer solution therein;

a lower buffer reservoir for holding said buffer solution;

a lower electrode within said lower buffer reservoir in electrical contact with said buffer solution;

means for separating said component from said mixture, said means being interposed between said first and second reservoirs, said means comprising:

a hollow frusto-conical outer member, an inner conical member spaced apart from an interior surface of said hollow frusto-conical outer member to form a column therebetween, said inner conical member including a cavity to provide additional heat exchange surface to remove heat from said column, and a separation medium within said column in electrical contact with said upper and lower electrodes, wherein said component is simultaneously concentrated while being separated from said mixture as said component migrates through said separation medium from a first end of said column to a second end thereof;

an elution chamber attached to said second end of said column for removing a separated and concentrated component from said separation medium; and recycle means for recycling said buffer solution in a path between said first and second buffer reservoirs without a formation of an electrical circuit across said path.

* * * * *